(12) United States Patent
Kusters et al.

(10) Patent No.: US 10,300,189 B2
(45) Date of Patent: May 28, 2019

(54) WHOLE BLOOD SEPARATION SYSTEM

(71) Applicant: Fenwal, Inc., Lake Zurich, IL (US)

(72) Inventors: Benjamin E. Kusters, Pleasant Prairie, WI (US); Kyungyoon Min, Kildeer, IL (US); Christopher J. Wegener, Libertyville, IL (US); Daniel R. Boggs, Libertyville, IL (US)

(73) Assignee: Fenwal, Inc., Lake Zurich, IL (US)

( * ) Notice: Subject to any disclaimer, the term of this patent is extended or adjusted under 35 U.S.C. 154(b) by 0 days.

(21) Appl. No.: 15/122,060

(22) PCT Filed: Apr. 30, 2014

(86) PCT No.: PCT/US2014/036011
§ 371 (c)(1),
(2) Date: Aug. 26, 2016

(87) PCT Pub. No.: WO2105/167487
PCT Pub. Date: Nov. 5, 2015

(65) Prior Publication Data
US 2017/0128656 A1 May 11, 2017

(51) Int. Cl.
*A61M 1/26* (2006.01)
*A61M 1/34* (2006.01)
(Continued)

(52) U.S. Cl.
CPC ........ *A61M 1/3496* (2013.01); *A61M 1/0218* (2014.02); *A61M 1/265* (2014.02);
(Continued)

(58) Field of Classification Search
CPC .. A61M 1/3496; A61M 1/265; A61M 1/0218; A61M 1/3633; A61M 2205/7563;
(Continued)

(56) References Cited

U.S. PATENT DOCUMENTS

| 4,871,462 A * | 10/1989 | Fischel ................. B01D 63/16 |
|---|---|---|
| | | 210/321.64 |
| 5,194,145 A | 3/1993 | Schoendorfer |
| (Continued) | | |

FOREIGN PATENT DOCUMENTS

| EP | 0 403 031 A2 | 12/1990 |
|---|---|---|
| WO | WO2014/039086 A1 | 3/2014 |

OTHER PUBLICATIONS

International Search Report, counterpart International Appl. No. PCT/US2014/036011 (dated Dec. 23, 2014), 4 pages.

*Primary Examiner* — Claire A Norris
*Assistant Examiner* — Julia L. Wun
(74) *Attorney, Agent, or Firm* — Cook Alex Ltd.

(57) ABSTRACT

A system and method are provided for controlling fouling and complement protein activation during separation of plasma from whole blood using a spinning membrane separator. The separator includes a pair of relatively rotating surfaces spaced apart to define a gap therebetween, with at least one of the surfaces comprising a membrane that allows plasma to pass therethrough but substantially prevents the passage of red cells. In accordance with the method, the membrane material and membrane fabrication technique are selected so as that the resulting membrane both resists fouling and complement protein activation. In a specific embodiment, the membrane is has a smooth surface and substantially linear pores. The pores have a nominal diameter of less than 2 microns (so as to exclude platelets) and preferably a diameter of from 0.6 microns to 0.8 microns, as may be obtained by use of track-etching. In addition, the membrane material preferably is polycarbonate, as it has been determined that polycarbonate does not activate complement proteins.

3 Claims, 2 Drawing Sheets

(51) Int. Cl.
- *B01D 63/16* (2006.01)
- *B01D 65/08* (2006.01)
- *B01D 71/50* (2006.01)
- *A61M 1/02* (2006.01)
- *B01D 71/34* (2006.01)
- *A61M 1/36* (2006.01)

(52) U.S. Cl.
CPC ............ *B01D 63/16* (2013.01); *B01D 65/08* (2013.01); *B01D 71/34* (2013.01); *B01D 71/50* (2013.01); *A61M 1/3633* (2013.01); *A61M 2202/0429* (2013.01); *A61M 2205/7563* (2013.01); *B01D 2315/02* (2013.01); *B01D 2321/2033* (2013.01)

(58) Field of Classification Search
CPC .. A61M 2202/0429; A61M 2202/0413; A61M 2202/0415; B01D 71/50; B01D 71/34; B01D 2321/2033; B01D 2321/00; B01D 65/08; B01D 63/16; B01D 2315/02
USPC .... 210/636, 767, 780, 782, 649, 650, 321.6, 210/321.67, 321.72, 500.21, 500.27, 210/500.4, 500.42; 422/527, 534, 535
See application file for complete search history.

(56) References Cited

U.S. PATENT DOCUMENTS

| | | |
|---|---|---|
| 2002/0033367 A1 | 3/2002 | Prince et al. |
| 2014/0010738 A1 | 1/2014 | Boggs et al. |
| 2014/0193833 A1* | 7/2014 | Srivastava ......... G01N 33/5005 435/7.4 |

* cited by examiner

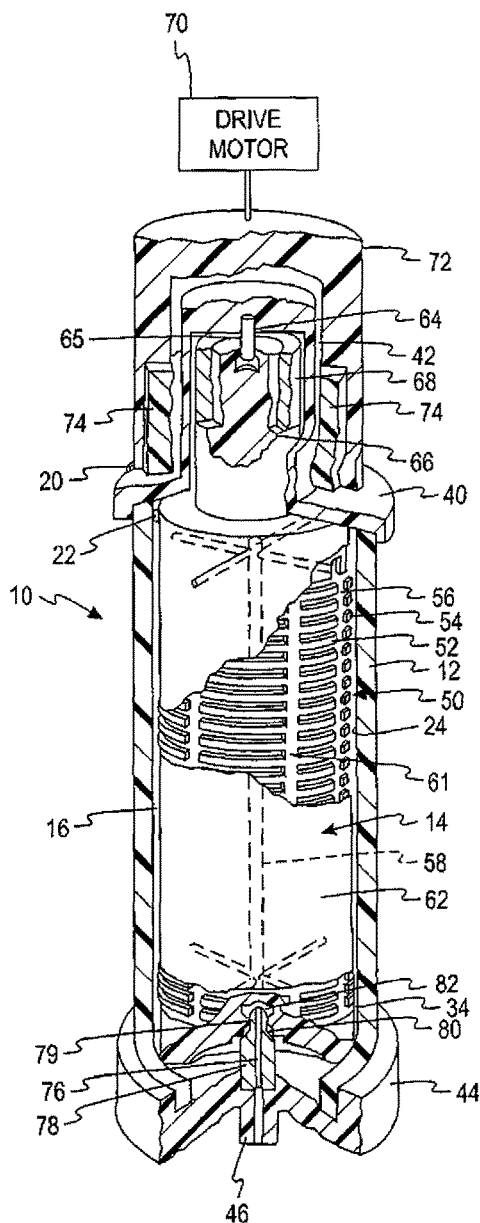
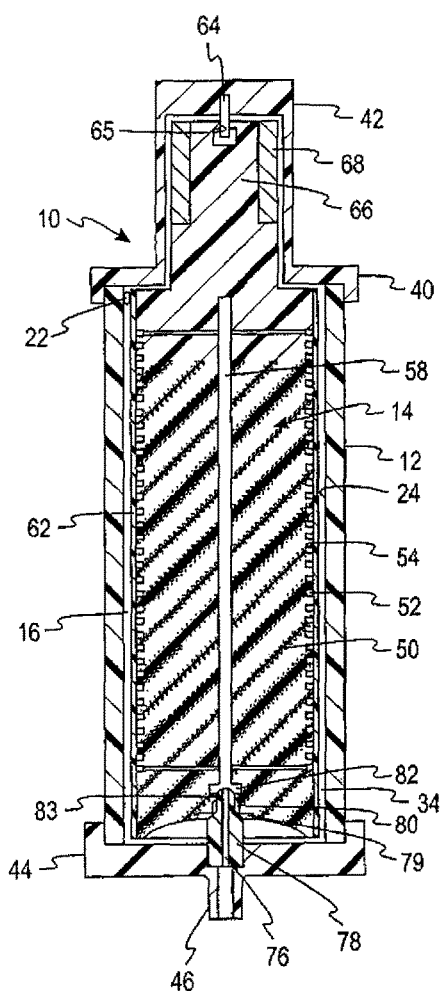
Fig. 1
Fig. 2

WHOLE BLOOD SEPARATION SYSTEM

The present application is the U.S. National Stage of PCT International Patent Application No. PCT/US2014/036011, filed on Apr. 30, 2014, the content of which are hereby incorporated herein by reference.

FIELD OF THE DISCLOSURE

The present application is related methods for filtration of plasma from whole blood using separation devices of the type employing relatively rotating surfaces, at least one of which carries a membrane for filtering plasma from whole blood passed between the surfaces.

BACKGROUND

There is class of devices, based on the use of a membrane, that has been used for plasmapheresis, that is separating plasma from whole blood. More specifically, this type of device employs relatively rotating surfaces, at least one or which carries a porous membrane. Typically the device employs an outer stationary housing and an internal spinning rotor covered by a porous membrane.

One such well-known plasmapheresis device is the Autopheresis-C® separator available from Fenwal, Inc., a Fresenius Kabi company, of Lake Zurich, Ill. A detailed description of a spinning membrane separator may be found in U.S. Pat. No. 5,194,145 to Schoendorfer, which is incorporated by reference herein. This patent describes a membrane-covered spinner having an interior collection system disposed within a stationary shell. Blood is fed into an annular space or gap between the spinner and the shell. The blood moves along the longitudinal axis of the shell toward an exit region, with plasma passing through the membrane and out of the shell into a collection bag. The remaining blood components, primarily red blood cells, platelets and white cells, move to the exit region between the spinner and the shell and then are typically returned to the donor.

Spinning membrane separators have been found to provide improved plasma filtration rates, due primarily to the unique flow patterns ("Taylor vortices") induced in the gap between the spinning membrane and the shell. The Taylor vortices create shear forces in the gap that help to keep the blood cells from depositing on and fouling or clogging the membrane, which otherwise would tend to decrease the rate of fluid flow through the membrane, thus increasing procedure times, and increase the transmembrane pressure, which could cause cell damage or device failure. Nevertheless, fouling or clogging of the membrane continues to be a limiting factor in efficiently performing plasmapheresis, and various methods for controlling fouling have been contemplated, including by optimizing the filtrate flow rate. See, e.g., US 2012/0273416, which is incorporated by reference herein.

The subject matter disclosed herein provides further advances in controlling the fouling or clogging of membrane separators for performing plasmapheresis.

SUMMARY OF THE DISCLOSURE

The present subject matter has a number of aspects which may be used in various combinations, and the disclosure of one or more specific embodiments is for the purpose of disclosure and description, and not limitation. This summary highlights only a few of the aspects of this subject matter, and additional aspects are disclosed in the drawings and the more detailed description that follows.

In accordance with one aspect of the present disclosure, a method is provided for controlling fouling and complement protein activation during separation of plasma from whole blood. The method includes providing a source of whole blood collected, and providing a blood separation circuit that comprises a separator including a pair of relatively rotating surfaces spaced apart to define a gap therebetween, with at least one of the surfaces comprising a membrane that allows plasma to pass therethrough but substantially prevents the passage of cellular components.

In accordance with the method, the membrane material and membrane fabrication technique are selected so as that the resulting membrane both resists fouling and complement protein activation. In a specific embodiment, the membrane has a smooth surface and substantially linear pores. The pores have a nominal diameter of less than 2 microns (so as to exclude platelets) and preferably a diameter of from 0.6 microns to 0.8 microns. Such precise linear pores may be formed by the track-etching process.

In addition, the membrane material preferably is polycarbonate, as it has been determined that polycarbonate does not activate complement proteins. However other polymeric materials that do not activate complement proteins (such as polyvinylidene fluoride or "PVDF") may also be used. When whole blood is flowed through the gap so that plasma passes through membrane and the cellular components are blocked from passage and concentrated within the gap, cellular material is less likely to adhere to the membrane surface, and the plasma flowing through the membrane is less likely to be degraded. The separated red cells are withdrawn from the gap, and then may be directed into a red cell storage container for storage and for subsequent administration to patients needing red cells, or returned to the donor.

Further, in connection with the subject matter described herein a pre-assembled disposable fluid flow circuit is described for separating whole blood into a plasma component and a concentrated red blood cell component. The fluid flow circuit, is preferably pre-assembled and pre-sterilized, and includes a whole blood fluid flow path. The fluid circuit includes a separator with an outer housing and an inner rotor mounted within the housing for rotation relative to the housing, with a gap defined between the outer surface of the rotor and an inner surface of the housing. At least one of the inner or outer surfaces of the housing and rotor, respectfully, comprises a filter membrane configured to allow passage of plasma therethrough while substantially blocking cellular components.

In accordance with the present disclosure, the membrane material and membrane fabrication technique are selected so as that the resulting membrane both resists fouling and complement protein activation. In a specific embodiment, the membrane has a smooth surface and substantially linear pores with a nominal diameter of less than 2 microns (so as to exclude platelets) and preferably a diameter of from 0.6 microns to 0.8 microns. Such precise linear pores may be formed by the track-etching process. Preferably, the membrane material is polycarbonate, as it has been determined that polycarbonate does not activate complement proteins. However other polymeric materials that do not activate complement (such as polyvinylidene fluoride or "PVDF") may also be used.

The outer housing includes an inlet in fluid communication with the whole blood and/or cell preservation solution flow paths and in flow communication with the gap between the interior rotor and the outer housing, for directing whole blood and/or cell preservation solutions into the gap. The housing includes an outlet communicating with the gap, for example, for removing concentrated red cells from the gap. The housing and/or the rotor also may include an outlet communicating with the side of membrane facing away from the gap for collecting fluid that passes through the membrane, such as plasma. Further, the housing outlet that communicates with the gap is preferably in flow communication with an outlet fluid flow path for connection to a red cell storage container which may be pre-assembled and pre-attached to the rest of the fluid circuit if desired.

BRIEF DESCRIPTION OF THE DRAWINGS

These and other features of the present subject matter are described in the following detailed description and shown in the attached figures, of which:

FIG. 1 is a perspective view a spinning membrane separator, in partial cross section and with portions removed to show detail.

FIG. 2 is a longitudinal cross sectional view of the spinning membrane separator of FIG. 1.

DETAILED DESCRIPTION

Figure 3:
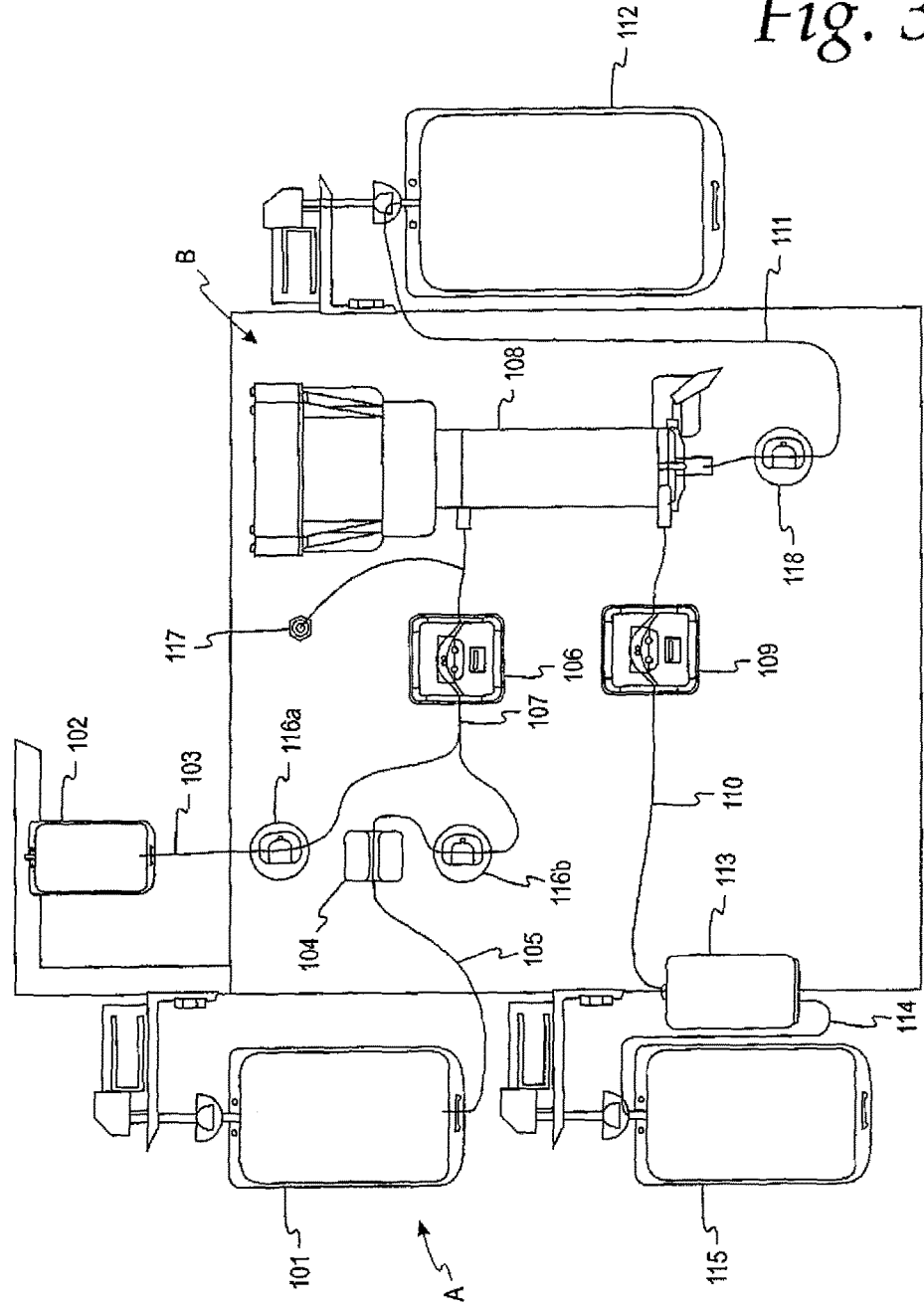
FIG. 3 is a schematic view of an automated whole blood separation system for processing previously-collected whole blood including a disposable fluid flow circuit module and a durable controller or control module with the fluid flow circuit module assembled thereon.

A more detailed description of the spinning membrane separator in accordance with the present disclosure and its use in various automated systems is set forth below. It should be understood that description below of specific devices and methods is intended to be exemplary, and not exhaustive of all possible variations or applications. Thus, the scope of the disclosure is not intended to be limiting, and should be understood to encompass variations or embodiments that would occur to persons of ordinary skill.

Turning to FIGS. 1 and 2, a spinning membrane blood separation or fractionation system, generally designated 10, is shown. Such a system 10 is typically used to extract plasma from whole blood obtained from an individual human donor. For ease of understanding, only the plasma separation device and the associated drive unit are shown, although it should be understood that such a separator forms part of a disposable system including collection bags, bags of additives such as saline or ACD, return bags, tubing, etc., and that there are also associated control and instrumentation systems for operation of the device.

The system 10 includes a generally cylindrical housing 12, mounted concentrically about a longitudinal vertical central axis. An internal member 14 is mounted concentric with the central axis. The housing and internal member is relatively rotatable. In the preferred embodiment, as illustrated, the housing is stationary and the internal member is a rotating spinner that is rotatable concentrically within the cylindrical housing 12. The boundaries of the blood flow path are generally defined by the gap 16 between the interior surface of the housing 12 and the exterior surface of the rotary spinner 14. The spacing between the housing and the spinner is sometimes referred to as the shear gap. A typical shear gap may be approximately 0.025-0.050 inches (0.067-0.127 cm) and may be of a uniform dimension along the axis, for example, where the axis of the spinner and housing are coincident. The shear gap may also vary circumferentially for example, where the axis of the housing and spinner are offset, or the shear gap may vary along the axial direction, for example preferably an increasing gap width in the direction of flow to limit hemolysis.

Whole blood is fed from an inlet conduit 20 through an inlet orifice 22, which directs the blood into the blood flow entrance region in a path tangential to the circumference about the upper end of the spinner 14. At the bottom end of the cylindrical housing 12, the housing inner wall includes an exit orifice 34.

The cylindrical housing 12 is completed by an upper end cap 40 having an end boss 42, the walls of which are nonmagnetic, and a bottom end housing 44 terminating in a plasma outlet orifice 46 concentric with the central axis.

The spinner 14 is rotatably mounted between the upper end cap 40 and the bottom end housing 44. The spinner 14 comprises a shaped central mandrel or rotor 50, the outer surface of which is shaped to define a series of spaced-apart circumferential grooves or ribs 52 separated by annular lands 54. The surface channels defined by the circumferential grooves 52 are interconnected by longitudinal grooves 56. At each end of the mandrel 50, these grooves 56 are in communication with a central orifice or manifold 58. In the illustrated embodiment, the surface of the rotary spinner 14 is at least partially, and is preferably substantially or entirely, covered by a cylindrical porous membrane 62.

The rotary spinner is mounted in the upper end cap to rotate about a pin 64, which is press fit into the end cap 40 on one side and seated within a cylindrical bearing surface 65 in an end cylinder 66 forming part of the rotary spinner 14. The internal spinner or outer housing may be rotated by any suitable rotary drive device or system. As illustrated, the end cylinder 66 is partially encompassed by a ring 68 of magnetic material utilized in indirect driving of the spinner 14. A drive motor 70 exterior to the housing 12 is coupled to turn an annular magnetic drive member 72 that includes at least a pair of interior permanent magnets 74. As the annular drive member 72 is rotated, magnetic attraction between the ring 68 interior to the housing 12 and the magnets 74 exterior to the housing locks the spinner 14 to the exterior drive, causing the spinner 14 to rotate.

At the lower end of the rotary spinner 14, the central outlet orifice 58 communicates with a central bore 76 in an end bearing 78 that is concentric with the central axis. An end bearing seat is defined by an internal shoulder 80 that forms a lower edge of a central opening 82. The central opening 82 communicates with the plasma outlet orifice 46. If the inner facing surface of the housing is covered entirely or partially by a membrane, a fluid collection or manifold may be provided beneath the membrane to collect plasma and direct it through a housing outlet (not shown).

As noted above, the surface of the rotary spinner 14 is at least partially, and is preferably substantially or entirely, covered by a cylindrical porous membrane 62. When used for separation of plasma from whole blood, the membrane 62 typically has a nominal pore size of 0.6 microns. Such plasmapheresis membranes have previously been made of a polyester mesh (substrate) with nylon particles solidified thereon, thereby creating a tortuous path through which only certain sized components will pass. It has been determined that the use of nylon mesh membranes for plasmaphereis tends to exacerbate fouling or clogging issues. Nylon membranes form their nominal pore size by creating a weave, resulting in a tortuous flow path through the membrane. Further, the surface of the membrane is highly irregular, and contains indentations or crevasses of 5 to 10 microns in size. As a result, plasma proteins are captured in the tortuous path through the membrane, while cellular debris tends to lodge in the irregular surface of the membrane, which tend to clog or foul the membrane.

Further, by limiting the fouling or clogging of the membrane, the rotational speed of the spinning membrane may be reduced, thus reducing the strength of the vortices and the consequent shear forces in the gap. This, in turn, reduces the likelihood of shear-induced hemolysis of the red blood cells, and in less free hemoglobin being present in the plasma and red cell products.

In addition, the nylon membrane material has been determined to initiate a cascade of complement protein activation within the plasma when passing through the membrane. Specifically, the nylon material of the membrane absorbs the fragmented form C3b of the complement protein C3 as plasma passes through the membrane in what is known as "Alternative Pathway" complement activation. Complement protein activation is undesirable in that the transfusion of fresh frozen plasma (FFP) having high levels of activated complement protein could result in a cascade of the complement system within the body, leading to an unnecessary inflammatory response In keeping with the present application, methods, systems and disposable flow circuits for separating plasma from whole blood utilizing spinning membrane separation are provided in which fouling or clogging and complement protein activation are reduced. This is accomplished by the use of an appropriate membrane material and membrane fabrication technique. In a specific embodiment, the membrane has a smooth surface and substantially linear or straight pores with a nominal diameter of less than 2 microns (so as to exclude platelets) and preferably a diameter of from 0.6 microns to 0.8 microns. Such precise linear pores may be formed by the track-etching process, in which polymeric materials are irradiated with energetic heavy ions, leading to the formation of linear damaged tracks across the polymeric film. These tracks are then revealed into pores by wet chemical etching, resulting in a porous membrane with randomly-distributed cylindrical pores and having a smooth surface. Consequently, cellular debris is less likely to adhere to the membrane surface and plasma proteins are better able to pass through the linear pore. Preferably, the membrane material is polycarbonate, as it has been determined that polycarbonate does not activate complement proteins. However other polymeric materials that do not activate complement proteins to the degree of nylon (such as polyvinylidene fluoride or "PVDF") may also be used.

While the use of track-etched polycarbonate membranes for cell washing applications is known, in such applications, the membranes have larger sized pores, typically 4-5 microns, to allow smaller cells, such as platelets, to pass through, while retaining larger cells, such as WBCs. In contrast, membranes used for plasmapheresis permit only plasma and plasma proteins allowed to pass through the membrane, while all cellular content is retained in the gap.

FIG. 3 illustrates one version of a potential system employing both a disposable fluid circuit module A and a reusable or durable controller module B. Although shown assembled, the fluid circuit module A and durable module B have separate and independent utility and may be used with other systems as well. As can be seen in FIG. 3, the disposable module A is conveniently mounted to the face of the reusable module B, which has associated hangars or supports, some of which may be associated with weight scales, for supporting the various containers of the disposable system. The disposable module is, as indicated earlier, preferably preassembled, and pre-sterilized. The cell preservative solution container may be pre-attached as part of the disposable system or may be added later, such as by a sterile connection device or other suitable attachment. A whole blood container which contains a unit of previously collected whole blood may also be pre-attached to the preassembled fluid circuit or attached by way of a sterile connection device or other suitable attachment mechanism. Alternatively, whole blood may be drawn directly from a donor.

The face of the reusable module B includes, in this embodiment, a separate solution clamp 116a for controlling flow of cell preservation solution from the solution container 102, which is hung from an elevated solution support pole. The whole blood container 101 is hung from a weight scale. The weight scale may be of conventional construction and may provide a weight measurement signal that may be used by the control system of the module B for sensing the amount of whole blood that remains in the container and/or the amount of whole blood that has been processed through the system. The disposable system includes a red cell flow path 105 that extends from the whole blood container, through the hematocrit detector 104, and through a separate whole blood clamp 116b for controlling flow of whole blood from the container into the system. The cell preservative solution flow path 103 and the whole blood flow path 105 combine at a junction, such as a v-site or y-site, upstream of the inlet pump 106. The combined flow path extends through the inlet pump and to an inlet on the separator device 108. The reusable module B includes a drive unit, such as a magnetic drive unit for causing rotation of the rotor within the separator housing without requiring drive members or components to physically extend through the housing. In this arrangement, the rotor includes a magnetically coupled drive element that is rotated by the magnetic drive unit associated with the reusable module. This system is described more fully in U.S. Pat. No. 5,194,145 to Schoendorfer, which was previously incorporated by reference herein.

The concentrated red cell outlet from the separator 108 is attached to the red cell flow path 110, which extends through outlet pump 109 and to an inlet into the optional leukocyte reduction filter 113. Filter media located between the inlet and outlet of the leukocyte reduction filter substantially removes leukocytes from the red cells. From the filter outlet, the red cell flow path tubing 114 conveys the red cells into the red cell collection container 115.

Plasma is conducted from the plasma outlet of the separator through a plasma flow control clamp 118 and into the plasma collection container 112. In a manner similar to the whole blood container, the concentrated red cell container 115 and the plasma container 112 are suspended from weight scales which may be in electronic communication with the control system of the durable or reusable module B to provide information regarding the amount of concentrated red cells and/or plasma collected from the whole blood or the rate of collection.

While this system has been illustrated with certain basic components and features as described above, this description is not intended to preclude the addition of other components, such as sensors, pumps, filters or the like as may be desired. For example, it may optionally be desired to filter plasma before it enters the plasma collection container or to omit a leukoreduction filter for red cells. Although the plasma removed from the separator 108 is largely cell free, there may be a further desire to filter the plasma for reasons of subsequent administration or processing. The present description is not intended to preclude the possible addition of further components or the deletion of one or more of the components described above.

Turning now to the processing of whole blood in the illustrated system, the separation process begins by priming the system. "Priming" refers to the method by which the filter membrane is prepared (i.e., wetted) prior to use. Wetting with a fluid helps to displace air present in the matrix of the membrane prior to pressure-induced fluid flow through the membrane. Typically, a low viscosity non-biological fluid, such as a cell preservation solution (red cell solution such as, Adsol® solution) is used for wetting to allow the most effective displacement of air. During the prime, fluid is removed from the cell preservation solution bag 102 by the inlet pump 106 until the solution line 103, whole blood line 105, inlet line 107, and spinning membrane device 108 are completely filled with the solution. To ensure proper priming, the inlet pump 106 may move both clockwise and counterclockwise during the prime. The purpose of the solution prime is to prevent an air-blood interface from forming by creating a solution-blood interface and to wet the membrane within the separation device. Each is a measure taken to reduce the hemolysis of red blood cells.

After the system is successfully primed, the cell solution flow path 103 will be closed by the inlet clamp 116. The illustrated inlet clamp is a binary clamp that can close either the cell preservation solution flow path 103 or the whole blood flow path 107. Whole blood will then be pumped through the whole blood flow path 105 and the inlet flow path 107 by the inlet pump 106 into the separator 108. Inlet pump 106 flow rates can vary from about 10 ml/min to 150 ml/min depending on desired product outcomes for a specific procedure. As the whole blood leaves the whole blood container 101 it will pass through the whole blood hematocrit detector 104 which will generate an estimation of the whole blood hematocrit through IR LED reflectance measurements. Details of the hematocrit detector are explained in U.S. Pat. No. 6,419,822, incorporated by reference herein. The whole blood hematocrit value is required for an initial control algorithm of the illustrated system, but may not be essential in other systems.

After whole blood has filled the separator 108, the system will begin to draw plasma from the separator which separates the whole blood entering the spinning membrane device into a red cell concentrate and virtually cell free plasma. Packed red blood cells at approximately 80-85% hematocrit will be pumped out of the separator 108 through the red cell flow path 110 and either collected or returned to the donor. If the red blood cells are to be collected, they are preferably pumped into the red blood cell leukofilter 113 by the outlet pump 109. The outlet pump forces the packed red blood cells through the red blood cell leukofilter 113 and the red cell concentrate which exits the red blood cell leukofilter 13 through the red blood cell line 114 and into the red blood cell product bag 115 will be successfully depleted of white blood cells and also depleted of platelets. It is also possible to complete a whole blood automated separation without the use of a red blood cell leukofilter 113. In this case the red blood cell leukofilter 114 would be removed from the system and the red blood cell product 115 would not be depleted of white blood cells or platelets.

Throughout the procedure, plasma will flow through the plasma flow path 111 into the plasma bag 112 at a flow rate equal to the difference between the inlet pump 106 flow rate and outlet pump 109 flow rate, as is currently done in other spinning membrane separation applications like that applied in the Autopheresis-C instrument referred to above. The pressure across the membrane generated by the offset in flow rates is monitored by the pressure sensor 117. The pressure measurements are used to control the plasma flow rate using the algorithm described in US 2012/0273416, which was previously incorporated by reference herein.

The system in FIG. 11 will continue to separate packed red blood cells and plasma until the whole blood bag 101 is empty as detected by air passing through the whole blood hematocrit detector 104. At this point the whole blood line 105 will be closed and the cell preservative solution line will be opened by the inlet clamp 116 to start the solution rinse or flush. During the solution rinse, preservative solution will be removed from the solution bag 102 and pumped into the separator 108 by the inlet pump 106. The plasma flow path 111 is closed by the plasma clamp 118 during the solution rinse. The solution rinse is used to flush any blood remaining in the system into the red blood cell product container 115. The solution rinse will also increase the red blood cell product container 115 volume to the level desired for proper red blood cell storage. After the solution rinse is finished the separation of the whole blood unit is complete.

Thus, an improved system and method for performing plasmapheresis using a spinning membrane separator are disclosed that results in less membrane fouling and complement protein activation. The description provided above is intended for illustrative purposes only, and is not intended to limit the scope of the disclosure to any specific method, system, or apparatus or device described herein.

The invention claimed is:

1. An automated whole blood separation system comprising a disposable fluid flow circuit and a durable controller configured to cooperate with and control flow through the disposable fluid flow circuit, the disposable fluid flow circuit comprising:

a whole blood fluid flow path with a whole blood inlet for connection to a source of whole blood;

a separator including outer housing and inner rotor mounted within the outer housing for rotation relative to the outer housing, a gap being defined between an outer surface of the rotor and an inner surface of the outer housing, at least one of the outer surface of the rotor or inner surface of the outer housing comprising a filter membrane configured to allow the passage of plasma therethrough while substantially blocking cellular components, the membrane consisting of polycarbonate and having a smooth surface and substantially linear pores with a nominal diameter of from 0.6 microns to 0.8 microns, the outer housing including an inlet in fluid communication with the whole blood fluid flow path, or a cell preservation solution fluid flow path, or the whole blood fluid flow path and the cell preservation solution fluid flow path, and in flow communication with the gap for directing whole blood, or cell preservation solution, or whole blood and cell preservation solution into the gap, the outer housing including an outlet communicating with the gap, and one of the outer housing and the rotor including an outlet communicating with the side of the membrane facing away from the gap; and the outlet in the outer housing communicating with the gap being in flow communication with an outlet fluid flow path for connection to a storage container.

2. A method controlling fouling and complement protein activation during spinning membrane filtration of plasma from whole blood comprising:

(a) providing a source of whole blood;

(b) providing a blood separation circuit comprising
a whole blood fluid flow path with a whole blood inlet for connection to a source of whole blood;
a separator including outer housing and inner rotor mounted within the outer housing for rotation relative to the outer housing, a gap being defined between an outer surface of the rotor and an inner surface of the outer housing, at least one of the outer surface of the rotor or inner surface of the outer housing comprising a filter membrane configured to allow the passage of plasma therethrough while substantially blocking cellular components, the membrane consisting of polycarbonate and having a smooth surface and substantially linear pores with a nominal diameter of from 0.6 microns to 0.8 microns, the outer housing including an inlet in fluid communication with the whole blood fluid flow path, or a cell preservation solution fluid flow path, or the whole blood fluid flow path and the cell preservation solution fluid flow path, and in flow communication with the gap for directing whole blood, or cell preservation solution, or whole blood and cell preservation solution into the gap, the outer housing including an outlet communicating with the gap, and one of the outer housing and the rotor including an outlet communicating with the side of the membrane facing away from the gap; and the outlet in the outer housing communicating with the gap being in flow communication with an outlet fluid flow path for connection to a storage container;
(c) flowing whole blood from the collected unit through the gap, to allow plasma to pass through the membrane and cellular components to be blocked;
(d) withdrawing concentrated red blood cells from the gap.

3. A disposable fluid flow circuit for separating whole blood into a plasma component and a concentrated red cell component, the circuit comprising:
a whole blood fluid flow path with a whole blood inlet for connection to a source of whole blood;
a separator including outer housing and inner rotor mounted within the housing for rotation relative to the outer housing, a gap being defined between an outer surface of the rotor and an inner surface of the outer housing, at least one of the outer surface of the rotor or inner surface of the housing comprising a filter membrane configured to allow the passage of plasma therethrough while substantially blocking cellular components, the membrane consisting of polycarbonate and having a smooth surface and substantially linear pores with a nominal diameter of from 0.6 microns to 0.8 microns, the outer housing including an inlet in fluid communication with the whole blood fluid flow path, or a cell preservation solution fluid flow path, or the whole blood fluid flow path and the cell preservation solution fluid flow path, and in flow communication with the gap for directing whole blood, cell preservation solution, or whole blood and cell preservation solution into the gap, the outer housing including an outlet communicating with the gap, and one of the outer housing and the rotor including an outlet communicating with the side of the membrane facing away from the gap; and
the outlet in the outer housing communicating with the gap being in flow communication with an outlet fluid flow path for connection to a storage container.

* * * * *